(12) United States Patent
Liu et al.

(10) Patent No.: US 10,072,066 B2
(45) Date of Patent: Sep. 11, 2018

(54) METHODS AND COMPOSITIONS FOR TREATMENT OF A BETA THALESSEMIA

(71) Applicant: Sangamo BioSciences, Inc., Richmond, CA (US)

(72) Inventors: Pei-Qi Liu, Richmond, CA (US); Andreas Reik, Richmond, CA (US); Lei Zhang, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 108 days.

(21) Appl. No.: 14/611,880

(22) Filed: Feb. 2, 2015

(65) Prior Publication Data

US 2015/0218253 A1     Aug. 6, 2015

Related U.S. Application Data

(60) Provisional application No. 61/935,219, filed on Feb. 3, 2014.

(51) Int. Cl.
| | |
|---|---|
| *C12N 5/071* | (2010.01) |
| *A61K 38/00* | (2006.01) |
| *C07H 21/02* | (2006.01) |
| *C12Q 1/68* | (2018.01) |
| *C07K 14/805* | (2006.01) |
| *A61K 35/28* | (2015.01) |
| *A61K 35/12* | (2015.01) |

(52) U.S. Cl.
CPC ........... *C07K 14/805* (2013.01); *A61K 35/28* (2013.01); *A61K 2035/124* (2013.01); *C07K 2319/81* (2013.01)

(58) Field of Classification Search
None
See application file for complete search history.

(56) References Cited

U.S. PATENT DOCUMENTS

| | | |
|---|---|---|
| 5,356,802 A | 10/1994 | Chandrasegaran |
| 5,420,032 A | 5/1995 | Marshall et al. |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas, III |
| 6,140,466 A | 10/2000 | Barbas, III et al. |
| 6,200,759 B1 | 3/2001 | Dove et al. |

(Continued)

FOREIGN PATENT DOCUMENTS

| | | |
|---|---|---|
| GB | 2338237 A | 12/1999 |
| WO | WO 98/37186 A1 | 8/1998 |

(Continued)

OTHER PUBLICATIONS

Zou. Site-specific gene correction of a point mutation in human iPS cells derived from an adult patient with sickle cell disease. Blood, Oct. 27, 2011_ vol. 118, No. 17.*

(Continued)

*Primary Examiner* — Yong D Pak
(74) *Attorney, Agent, or Firm* — Pasternak Patent Law; Susan Abrahamson

(57) ABSTRACT

Methods and compositions for treatment of a beta thalessemia are provided.

12 Claims, 6 Drawing Sheets

Specification includes a Sequence Listing.

(56) References Cited

U.S. PATENT DOCUMENTS

| | | |
|---|---|---|
| 6,242,568 B1 | 6/2001 | Barbas, III et al. |
| 6,410,248 B1 | 6/2002 | Greisman et al. |
| 6,453,242 B1 | 9/2002 | Eisenbarg et al. |
| 6,479,626 B1 | 11/2002 | Kim et al. |
| 6,503,717 B2 | 1/2003 | Case et al. |
| 6,534,261 B1 | 3/2003 | Cox et al. |
| 6,599,692 B1 | 6/2003 | Case et al. |
| 6,607,882 B1 | 8/2003 | Cox et al. |
| 6,689,558 B2 | 2/2004 | Case |
| 6,794,136 B1 | 9/2004 | Eisenberg et al. |
| 6,824,978 B1 | 11/2004 | Cox et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,629,326 B2 | 12/2009 | Choulika et al. |
| 7,888,121 B2 | 2/2011 | Urnov et al. |
| 7,914,796 B2 | 3/2011 | Miller et al. |
| 7,972,854 B2 | 4/2011 | Miller et al. |
| 7,951,925 B2 | 5/2011 | Ando et al. |
| 8,034,598 B2 | 10/2011 | Miller et al. |
| 8,110,379 B2 | 2/2012 | DeKelver et al. |
| 8,153,773 B2 | 4/2012 | Jemielity et al. |
| 8,309,356 B2 * | 11/2012 | Glazer ............ A61K 48/005 435/463 |
| 8,409,861 B2 | 4/2013 | Guschin et al. |
| 8,420,782 B2 | 4/2013 | Bonas et al. |
| 8,440,431 B2 | 5/2013 | Voytas et al. |
| 8,586,526 B2 | 11/2013 | Gregory et al. |
| 8,623,618 B2 | 1/2014 | Doyon et al. |
| 8,921,332 B2 | 12/2014 | Choulika et al. |
| 9,267,123 B2 * | 2/2016 | Jaenisch ............ C12N 9/22 |
| 2003/0051270 A1 | 3/2003 | Kmiec et al. |
| 2003/0124581 A1 | 7/2003 | Dobrowolski et al. |
| 2003/0232410 A1 | 12/2003 | Liljedahl et al. |
| 2005/0026157 A1 | 2/2005 | Baltimore |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li |
| 2006/0188987 A1 | 8/2006 | Guschin |
| 2007/0117128 A1 | 5/2007 | Smith et al. |
| 2007/0141038 A1 | 6/2007 | Choulika et al. |
| 2007/0218528 A1 | 9/2007 | Miller |
| 2008/0159996 A1 | 4/2008 | Ando et al. |
| 2008/0299580 A1 | 12/2008 | DeKelver et al. |
| 2009/0068164 A1 | 3/2009 | Segal et al. |
| 2009/0117617 A1 | 5/2009 | Holmes et al. |
| 2010/0047805 A1 | 2/2010 | Wang |
| 2010/0218264 A1 | 8/2010 | Cui et al. |
| 2011/0041195 A1 | 2/2011 | Doyon |
| 2011/0207221 A1 | 8/2011 | Cost et al. |
| 2011/0265198 A1 | 10/2011 | Gregory et al. |
| 2011/0281361 A1 | 11/2011 | DeKelver et al. |
| 2011/0287512 A1 | 11/2011 | Paschon et al. |
| 2011/0301073 A1 | 12/2011 | Gregory et al. |
| 2012/0017290 A1 | 1/2012 | Cui et al. |
| 2012/0195936 A1 | 8/2012 | Rudolph et al. |
| 2012/0230971 A1 | 10/2012 | Choulika et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0326645 A1 | 12/2013 | Cost et al. |
| 2014/0080216 A1 * | 3/2014 | Cost ............ C07K 14/4702 435/462 |
| 2014/0093913 A1 | 4/2014 | Cost et al. |
| 2015/0056705 A1 | 2/2015 | Conway et al. |

FOREIGN PATENT DOCUMENTS

| | | |
|---|---|---|
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 00/46386 A3 | 2/2000 |
| WO | WO 00/27878 A1 | 5/2000 |
| WO | WO 01/88197 A2 | 11/2001 |
| WO | WO 02/016536 A1 | 2/2002 |
| WO | WO 02/077227 A2 | 10/2002 |
| WO | WO 07/014275 A2 | 2/2007 |
| WO | WO 03/016496 A2 | 2/2008 |
| WO | WO 09/042163 A2 | 4/2009 |
| WO | WO 10/079430 A1 | 7/2010 |
| WO | 2012094132 A1 | 7/2012 |
| WO | WO 13/019475 A1 | 2/2013 |
| WO | 2014036219 A2 | 3/2014 |

OTHER PUBLICATIONS

Argast, et al., "I-PPOI and I-CREI Homing Site Sequence Degeneracy Determined by Random Mutagenesis and Sequential In Vitro Enrichment," *J. Mol. Biol.* 280:345-353 (1998).

Ashworth, et al., "Computational Redesign of Endonuclease DNA Binding and Cleavage Specificity," *Nature* 441:656-659 (2003).

Beerli, et al., "Engineering Polydactyl Zinc-Finger Transcription Factors," *Nature Biotechnol.* 20:135-141 (2002).

Belfort, et al., "Homing Endonucleases: Keeping the House in Order," *Nucleic Acids Res.* 25:3379-3388 (1997).

Bitinaite, et al., "FOKI Dimerization Is Required for DNA Cleavage," *PNAS USA* 95:10,570-10,575 (1998).

Boch.' et al., "Breaking the Code of DNA Binding Specificity of TAL-Type III Effectors," *Science* 326:1509-1512 (2009).

Bonas, et al., "Genetic and Structural Characterization of the Avirulence Gene AVRBS3 From Xanthomonas Campestris PV. Vesicatoria," *Mol. Gen. Genet.* 218:127-136 (1989).

Chevalier, et al., "Design, Activity, and Structure of a Highly Specific Artificial Endonuclease," *Molecular Cell* 10:895-905 (2002).

Choo, et al., "Advances in Zinc Finger Engineering," *Curr. Opin. Struct. Biol.* 10:411-416 (2000).

Dujon, et al., "Mobile Introns: Definition of Terms and Recommended Nomenclature," *Gene* 82:115-118(1989).

Epinat, et al., "A Novel Engineered Meganuclease Induces Homologous Recombination in Yeast and Mammalian Cells," *Nucleic Acids Research* 31(11):3252-2962 (2003). doi: 10.1093/nar/gkg375.

Giarratana, et al., "Proof of Principle for Transfusion of In Vitro-Generated Red Blood Cells," *Blood* 118(19):5071-5079 (2011).

Gimble, et al., "Substrate Recognition and Induced DNA Distortion by the Pi-Scei Endonuclease, An Enzyme Generated by Protein Splicing," *J. Mol. Biol.* 263:163-180 (1996).

Grossman, et al., "Successful Ex Vivo Gene Therapy Directed to Liver in a Patient With Familial Hypercholesterolaemia," *Nature Genetics* 6:335-341 (1994) doi:10.1038/ng0494-335.

Guschin, et al., "A Rapid and General Assay for Monitoring Endogenous Gene Modification," *Methods Mol. Biol.* 649:247-256 (2010).

Haft, et al., "A Guild of 45 CRISPR-Associated (CAS) Protein Families and Multiple CRISPR/CAS Subtypes Exist in Prokaryotic Genomes," *PLoS Comput. Biol.* 1:e60 (2005).

Heuer, et al.. "Repeat Domain Diversity of AVRBS3-Like Genes in Ralstonia Solanacearum Strains and Association With Host Preferences in the Field," *Appl. and Envir. Micro.* 73:4379-4384 (2007).

Isalan, et al., "A Rapid, Generally Applicable Method to Engineer Zinc Fingers Illustrated by Targeting the W-1 Promoter," *Nature Biotechnology* 19(7):656-660 (2001).

(56) References Cited

OTHER PUBLICATIONS

Jansen, et al., "Identification of Genes That Are Associated With DNA Repeats in Prokaryotes," *Molecular Microbiology* 43(6):1565-1575 (2002).
Jasin, et al., "Genetic Manipulation of Genomes With Rare-Cutting Endonucleases," *Trends Genet.* 12:224-228 (1996).
Kay, et al., "A Bacterial Effector Acts as a Plant Transcription Factor and Induces a Cell Size Regulator," *Science* 318:648-651 (2007).
Kazazian and Boehm "Molecular Basis and Prenatal Diagnosis of Beta-Thalassemia," *Blood* 71(4):1107-1116 (1988).
Kierlin-Duncan, et at, "Using 5'-PTMS to Repair Mutant b-Globin Transcripts," *RNA* 13:1317-1327 (2007).
Kim, et al., "Insertion and Deletion Mutants of FOKI Restriction Endonuclease," *J. Biol. Chem.* 269:31978-31982 (1994).
Kim, et al., "Chimeric Restriction Endonuclease," *PNAS USA* 91:883-887 (1994).
Kormann, et al., "Expression of Therapeutic Proteins After Delivery of Chemically Modified MRNA in Mice," *Nature Biotechnology* 29(2):154-157 (2011).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Makarova, et al., "A DNA Repair System Specific for Thermophilic Archaea and Bacteria Predicted by Genomic Context Analysis," *Nucleic Acids Res.* 30:482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Moscou, et al., "A Simple Cipher Governs DNA Recognition by TAL Effectors," *Science* 326:1501 (2009).
Olovnikov, et al., "Bacterial Argonaute Samples the Transcriptome to Identify Foreign DNA," *Mol. Cell.* 51:594 (2013).
Pabo, et al., "Design and Selection of Novel CYS2HIS2 Zinc Finger Proteins," *Ann. Rev. Biochem.* 70:313-340 (2001).
Paques, et al.. "Meganucleases and DNA Double-Strand Break Induced Recombination: Persectives for Gene Therapy," *Current Gene Therapy* 7:49-66 (2007).
Perez, et al., "Establishment of HIV-1 Resistance in CD4+ T Cells by Genome Editing Using Zinc-Finger Nucleases," 26(7):808-816 (2008).
Perler, et al., "Protein Splicing Elements: Inteins and Exteins A Definition of Terms and Recommended Nomenclature," *Nucleic Acids Research* 22:1125-1127 (1994).
Roberts, et al., Rebase: Restriction Enzymes and Methyltransferases, *Nucleic Acids Res.* 31:418-420 (2003).
Schomack, et al., "Gene-For-Gene-Mediated Recognition of Nuclear-Targeted AVRBS3-Like Bacterial Effector Proteins," *J. Plant Physiol.* 163:256-272 (2006).
Segal, et al., "Custom DNA-Binding Proteins Come of Age: Polydactyl Zinc-Finger Proteins," *Curr. Opin. Biotechnol* 12(6):632-637 (2001).
Sheng, et al., "Structure-Based Cleavage Mechanism of Thermus Thermophilus Argonaute DNA Guide Strand-Mediated DNA Target Cleavage," *PNAS USA* 11:652 (2014).
Swarts, et al., "DNA-Guided DNA Interference by a Prokaryotic Argonaute," *Nature* 507(7491):258-261 (2014).
Tebas, et al., "Gene Editing of CCR5 in Autologous CD4 T Cells of Persons Infected With HIV," *New Engl. J. Med.* 370(10):901 (2014)
Urnov, et al., "Highly Efficient Endogenous Human Gene Correction Using Designed Zinc-Finger Nucleases," *Nature* 435(7042):646-651(2005).
Vogel, "A Bacterial Seek-And-Destroy System for Foreign DNA," *Science* 344(6187):972-973 (2014).
Voon, et al., "SiRNA-Mediated Reduction of A-Globin Results in Phenotypic Improvements in B-Thalassemic Cells," *Haematologica* 93(8):1288 (2008).
Yang, et al., "Purification, Cloning, and Characterization of the Cel I Nuclease," *Biochemistry* 39:3533-3541 (2000).
Yuan, et al., "Crystal Structure of A. Aeolicus Argonaute, a Site-Specific DNA-Guided Endoribonuclease, Provides Insights Into RISC-Mediated MRNA Cleavage," *Mol. Cell.* 19:405-419 (2005).
U.S. Appl. No. 60/118,669, filed Feb. 3, 1999.
Blobel, et al., "An International Effort to Cure a Global Health Problem: A Report on the 19th Hemoglobin Switching Conference," Experimental Hematology, 43(1):821-837 (2015).
Hoban, et al., "Zinc Finger Nucleases Targeting the β-Globin Locus Drive Efficient Correction of the Sickle Mutation in CD34+ Cells," Blood, The American Society of Hematology, 122:2904 (2013).
Lonkar, et al., "Targeted Correction of a Thalassemia-Associated β-Globin Mutation Induced by Pseudo-Complementary Peptide Nucleic Acids," Nucleic Acids Research, 37(11):3635-3644 (2009).
Raja, et al., "Recent Advances in Gene Therapy for Thalassemia," J Pharm Bioallied Sci, 4(3):194-201 (2012).
Sangamo BioSciences, Inc. "Sangamo Biosciences Announces First Presentation of Data From ZFP Therapeutic Program for Treatment of Sickle Cell Disease and Beta-Thalassemia at American Society of Hematology Meeting," www.prnewswire.com/news-release (2013).

\* cited by examiner

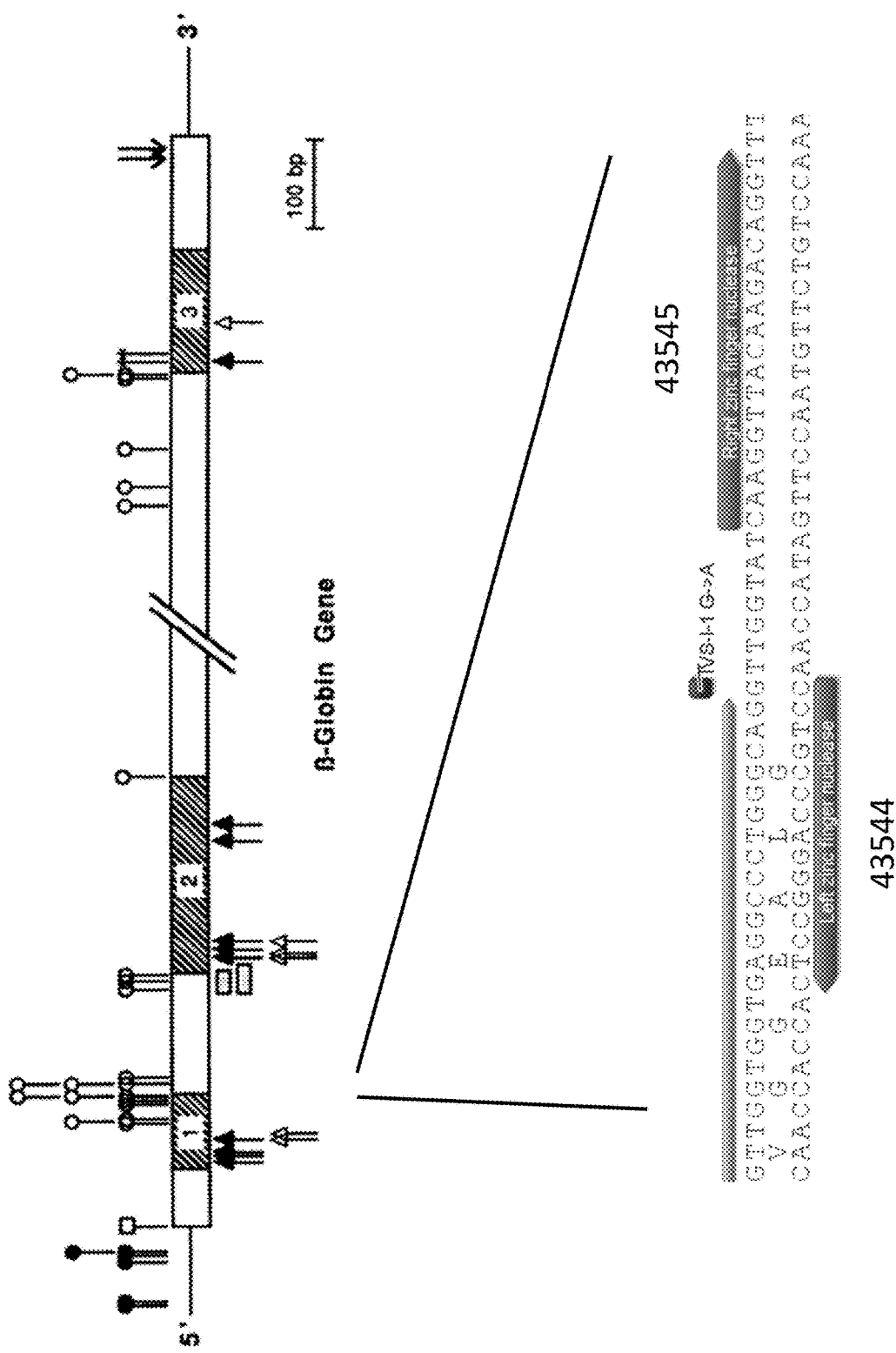

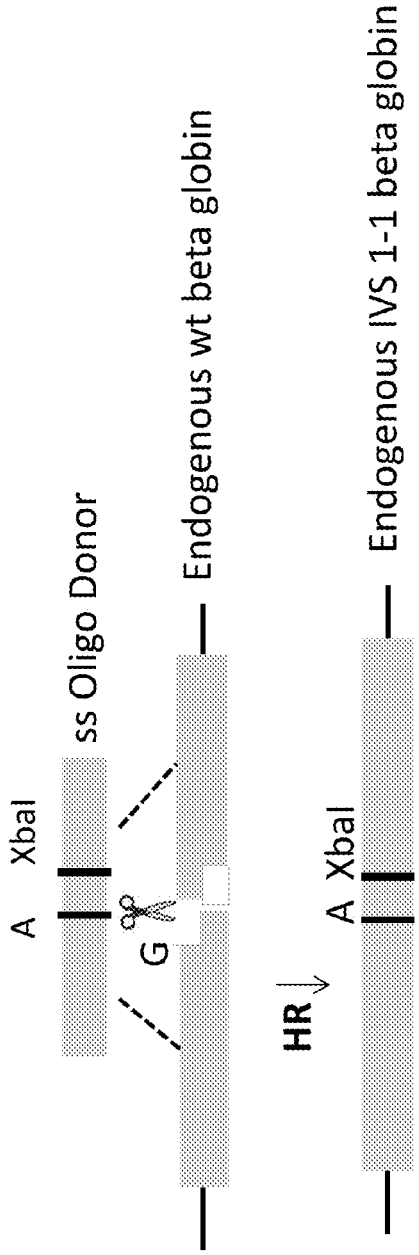

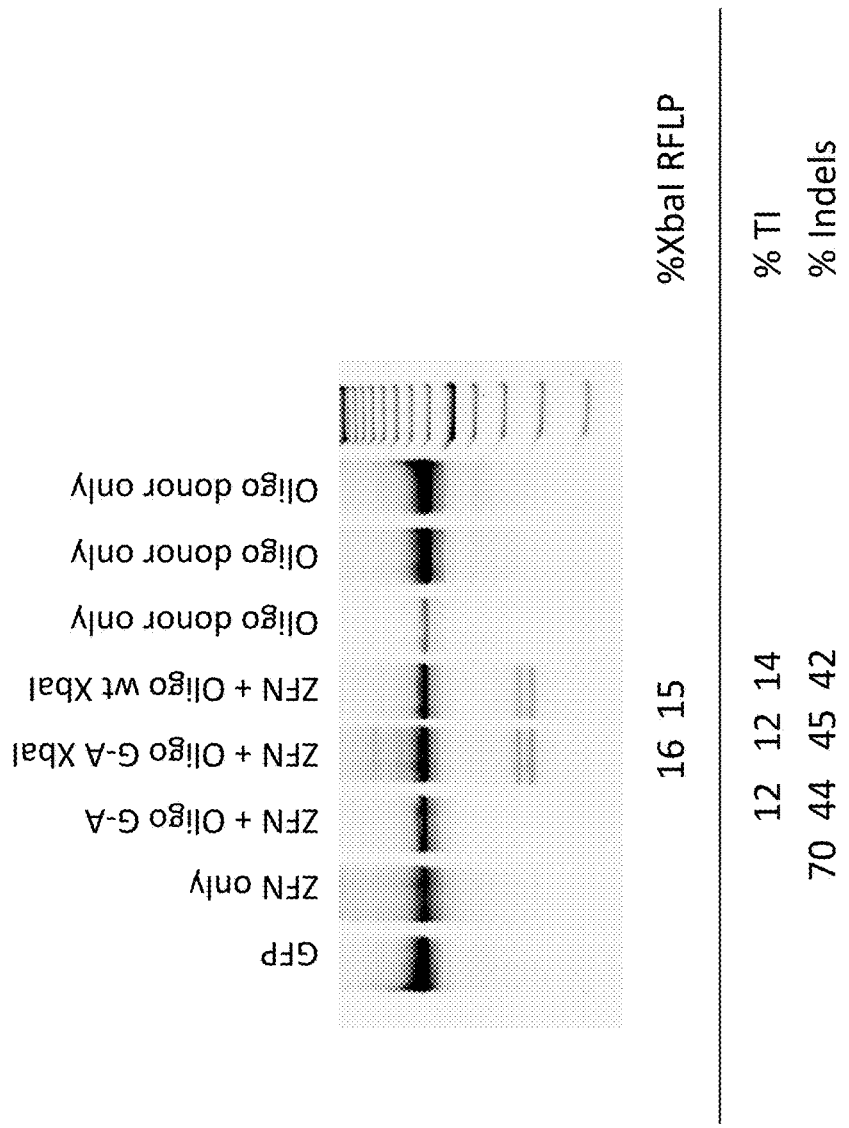

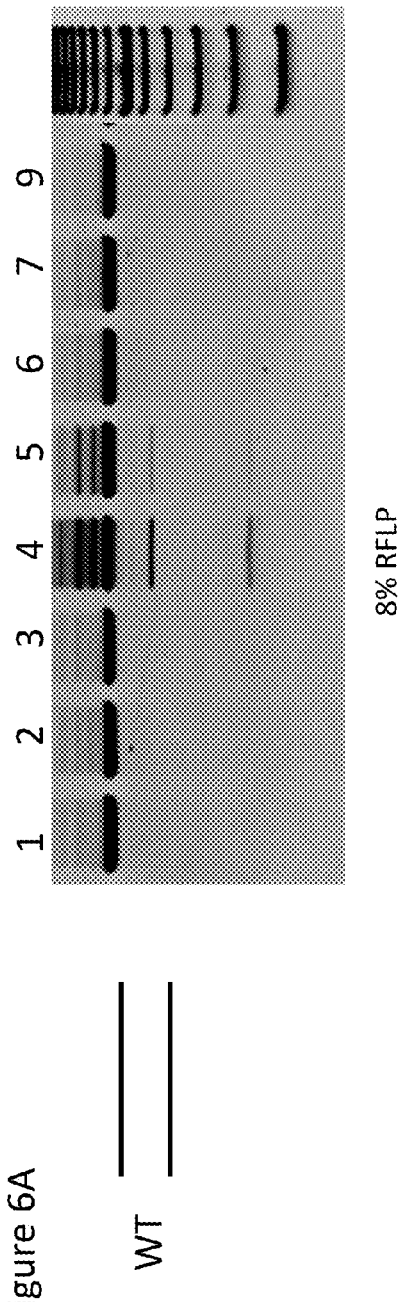
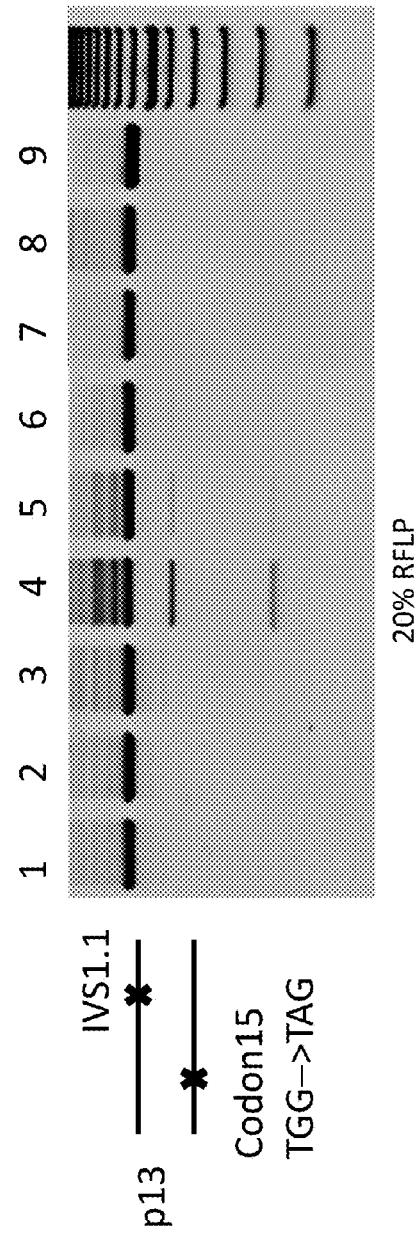

METHODS AND COMPOSITIONS FOR TREATMENT OF A BETA THALESSEMIA

CROSS-REFERENCE TO RELATED APPLICATIONS

The present application claims the benefit of U.S. Provisional Application No. 61/935,219, filed Feb. 3, 2014, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Feb. 23, 2015, is named 83280117_SL.txt and is 6,535 bytes in size.

TECHNICAL FIELD

The present disclosure is in the field of genome engineering of hematopoietic stem cells, especially for the treatment of a hemoglobinopathy such as beta thalessemia.

BACKGROUND

Gene therapy holds enormous potential for a new era in human medicine. These methodologies will allow treatment for conditions that heretofore have not been addressable by standard medical practice. One area that is especially promising is the ability to genetically engineer a cell to cause that cell to express a product not previously being produced in that cell, for example due to a mutation that inactivates the cognate gene in its genome. Examples of uses of this technology include the targeted correction of a disease-causing mutation, insertion of a gene encoding a novel therapeutic protein, insertion of a coding sequence encoding a protein that is lacking in the cell or in the individual, insertion of a wild type gene in a cell containing a mutated gene sequence, and insertion of a sequence that encodes a structural nucleic acid such as a microRNA or siRNA.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., co-owned U.S. Pat. No. 7,888,121). Nucleases specific for targeted genes can be utilized such that the transgene construct is inserted by either homology directed repair (HDR) or by end capture during non-homologous end joining (NHEJ) driven processes. Targeted loci include "safe harbor" loci for example a CCR5 gene, a CXCR4 gene, a PPP1R12C (also known as AAVS1) gene, an albumin gene or a Rosa gene. See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960). Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes. Nucleases include zinc finger nucleases (ZFN), transcription activator like effector nucleases (TALENs), mega or homing endonucleases, nuclease systems such as CRISPR/Cas that use a guide RNA to determine specificity, and fusions between nucleases such as mega-TALs.

Nuclease-mediated targeted integration can also be used for targeted gene correction of an endogenous locus. Gene correction can occur following nuclease cleavage as above by inserting a transgene of interest into the mutant endogenous locus. Alternatively, a mutant gene can be corrected by integrating a portion of the wild type or engineered sequence to replace (correct) the mutant portion of the gene locus. For gene correction, as with targeted integration of any exogenous sequence, sequence specific nucleases are used (e.g., ZFN, TALENs, CRISPR/Cas, meganucleases or megaTALs) to introduce a DSB in the endogenous gene of interest and a donor, typically comprising homology arms to the endogenous (mutant) gene, is integrated such that the endogenous (mutant) gene is altered by the donor. This approach can be used to correct mutations within an endogenous gene sequence and/or to insert engineered sequences for a desired purpose.

Red blood cells (RBCs), or erythrocytes, are the major cellular component of blood. In fact, RBCs account for one quarter of the cells in a human. Mature RBCs lack a nucleus and many other organelles in humans, and are full of hemoglobin, a metalloprotein found in RBCs that functions to carry oxygen to the tissues as well as carry carbon dioxide out of the tissues and back to the lungs for removal. The protein makes up approximately 97% of the dry weight of RBCs and it increases the oxygen carrying ability of blood by about seventy fold. Hemoglobin is a heterotetramer comprising two α-like globin chains and two β-like globin chains and 4 heme groups. In adults the α2β2 tetramer is referred to as Hemoglobin A (HbA) or adult hemoglobin. Typically, the alpha and beta globin chains are synthesized in an approximate 1:1 ratio and this ratio seems to be critical in terms of hemoglobin and RBC stabilization. In fact, in some cases where one type of globin gene is inadequately expressed (see below), reducing expression (e.g. using a specific siRNA) of the other type of globin, restoring this 1:1 ratio, alleviates some aspects of the mutant cellular phenotype (see Voon et at (2008) *Haematologica* 93(8):1288). In a developing fetus, a different form of hemoglobin, fetal hemoglobin (HbF) is produced which has a higher binding affinity for oxygen than Hemoglobin A such that oxygen can be delivered to the baby's system via the mother's blood stream. Fetal hemoglobin also contains two α globin chains, but in place of the adult β-globin chains, it has two fetal γ-globin chains (i.e., fetal hemoglobin is α2γ2). At approximately 30 weeks of gestation, the synthesis of γ globin in the fetus starts to drop while the production of β globin increases. By approximately 10 months of age after birth, the newborn's hemoglobin is nearly all α2β2 although some HbF persists into adulthood (approximately 1-3% of total hemoglobin). The regulation of the switch from production of γ to β is quite complex, and primarily involves an expressional down-regulation of γ globin with a simultaneous up-regulation of β globin expression.

Genetic defects in the sequences encoding the hemoglobin chains can be responsible for a number of diseases known as hemoglobinopathies, including sickle cell anemia and thalassemias. In the majority of patients with hemoglobinopathies, the genes encoding γ globin remain intact, but γ globin expression is relatively low due to normal gene repression occurring around parturition as described above.

Thalassemias are also diseases relating to hemoglobin and typically involve a reduced production of globin chains. This can occur through mutations in the regulatory regions of the genes or from a mutation in a globin coding sequence that results in reduced production. Alpha thalassemias are associated with people of Western Africa and South Asian descent, and may confer malarial resistance. Beta thalassemia is associated with people of Mediterranean descent, typically from Greece and the coastal areas of Turkey and Italy. Treatment of thalassemias usually involves blood transfusions and iron chelation therapy. Bone marrow transplants are also being used for treatment of people with severe thalassemias if an appropriate donor can be identified, but this procedure can have significant risks. Beta thalassemias are divided generally into three groups: i) Thalassemia trait or minor, where the patients are either carriers of a thalassemia disease allele or have very mild symptoms that may result in a mild anemia. ii) Thalassemia intermedia patients, where the lack of beta globin is great enough to cause a moderately severe anemia and significant health problems, including bone deformities and enlargement of the spleen. However, there is a wide range in the clinical severity of this condition, and the borderline between thalassemia intermedia and the most severe form, thalassemia major, can be confusing. The deciding factor seems to be the amount of blood transfusions required by the patient. iii) Thalassemia Major or Cooley's Anemia. This is the most severe form of beta thalassemia in which the complete lack of beta globin causes a life-threatening anemia that requires regular blood transfusions and extensive ongoing medical care. These extensive, lifelong blood transfusions lead to iron-overload which must be treated with chelation therapy to prevent early death from organ failure.

For beta thalessemias, in the late 1980s, it was estimated that approximately 54 mutations in the beta globin gene encompassed all known diseased beta globin genes; the number has since grown to over 200. The mutations are broken down into mutations which result in non-functional beta globin protein, including nonsense mutations and frameshift mutations; RNA processing mutations, including changes in the splice junctions and changes in splice consensus sequences as well as changes in internal intronic and exonic sequences that result in aberrant splicing; transcriptional mutants; polyA and RNA cleavage mutants; cap site mutants; and unstable mRNA mutants. These mutations result in either complete loss of beta globin mRNA in the cell (also referred to as "β–0") or a reduced level of expression and mRNA accumulation (referred to as "β+"). (see, e.g., Kazazian and Boehm (1988) *Blood* vol 71 No 4: 1107). Patients with the milder β+ forms of beta thalassemia may have relatively normal lifespans, but those with the severe β–0 forms may die before age 30 if untreated, and if iron levels are not managed may also have a similarly shortened life span if given frequent transfusions. Of note, some specific mutations are more common than others; in particular, in some parts of Europe and the Middle East, a mutation known as "IVS1-1" (which stands for "intervening sequence 1, mutation number 1") accounts for approximately 20% of all b-thalassemia major mutations. In this mutation, the "GT" dinucleotide at the beginning of intron 1 of the human beta-globin gene is changed to an "AT," thereby disrupting a key signal (known as the "splice donor motif") essential for accurate and efficient removal of the intron 1 from the beta-globin pre-mRNA. As a result, a significant reduction in beta-globin protein is observed during erythropoiesis, resulting in transfusion-dependent b-thalassemia major.

Thus, there remains a need for additional methods and compositions that can be used for genome editing, to correct an aberrant gene or alter the expression of others for example to treat beta thalassemias.

SUMMARY

Disclosed herein are methods and compositions for altering the expression of and/or for correcting one or more genes encoding proteins involved in a genetic disease (e.g., producing proteins lacking, deficient or aberrant in the disease and/or proteins that regulate these proteins) such as hemoglobinopathies (e.g., beta thalassemias). Alteration of such genes can result in the treatment of these genetic diseases (e.g., beta thalassemias). In particular, genome editing is used to correct an aberrant gene, insert a wild type gene, or change the expression of an endogenous gene. By way of non-limiting example, a mutated gene encoding β globin may be corrected in a cell to produce a wild type β globin protein in the cell to treat a hemoglobinopathy caused by the faulty β globin gene. One approach further involves the use of modification of a stem cell (e.g., hematopoietic stem cell or RBC precursor), which stem cell can then be used to engraft into a patient, for treatment of a hemoglobinopathy.

In one aspect, described herein is a nuclease protein or system (e.g., ZFN, TALEN, mega or homing endonuclease, mega-TAL or a CRISPR/Cas system) that binds to target site in a region of interest (e.g., a β globin gene) in a genome, wherein the nuclease comprises one or more engineered domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. In another embodiment, the nuclease is a TALE nuclease (TALEN) that cleaves a target genomic region of interest, wherein the TALEN comprises one or more engineered TALE DNA binding domains and a nuclease cleavage domain or cleavage half-domain. In another embodiment, the nuclease is a CRISPR/Cas system wherein the specificity of the CRISPR/Cas is determined by an engineered single guide mRNA. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the DNA binding domain (e.g. zinc finger or TALE DNA binding domain) recognizes a target site in a beta globin gene. In certain embodiments, the zinc finger domain comprises 5 or 6 zinc finger domains and recognizes a target site in a globin gene.

In another aspect, described herein is a CRISPR/Cas system that binds to target site in a region of interest (e.g., a highly expressed gene, a disease associated gene or a safe harbor gene) in a genome, wherein the CRISPR/Cas system comprises a CRIPSR/Cas nuclease and an engineered crRNA/tracrRNA (or single guide RNA). In certain embodiments, the CRISPR/Cas system recognizes a target site in a highly expressed, disease associated, or safe harbor gene. In certain embodiments, the CRISPR/Cas system recognizes a target in a beta globin gene.

The ZFNs, TALENs and/or CRISPR/Cas system as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the ZFNs, TALENs and/or CRISPR/Cas system bind(s) to and/or cleave(s) a globin gene. In other embodiments, the ZFNs, TALENs and/or CRISPR/Cas system binds to and/or cleaves a safe-harbor gene, for example a CCR5 gene, a CXCR4 gene, a PPP1R12C (also known as AAVS1) gene, an albumin gene, an HPRT gene or a Rosa gene. See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960. In addition, to aid in selection, the HPRT locus may be used (see U.S. Patent Publication No. 20130122591). In another aspect, described herein are compositions comprising one or more of the zinc-finger and/or TALE nucleases or CRISPR/Cas system as described herein. In some embodiments, the ZFNs, TALENs and/or CRISPR/Cas system binds to and cleaves a β or globin gene. In another aspect, described herein are compositions comprising one or more of the zinc-finger, TALE or Cas nucleases as described herein.

In another aspect, described herein is a polynucleotide encoding one or more ZFNs, TALENs and/or CRISPR/Cas system as described herein. The polynucleotide may be, for example, mRNA. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012-0195936).

In another aspect, described herein is a ZFN, TALEN and/or CRISPR/Cas system expression vector comprising a polynucleotide, encoding one or more ZFNs, TALENs and/or CRISPR/Cas system described herein, operably linked to a promoter. In one embodiment, the expression vector is a viral vector.

In one aspect, described herein is a ZFN, TALEN and/or CRISPR/Cas system protein that is used to cleave a target DNA.

In another aspect, described herein is a genetically modified cell or cell line, for example as compared to the wild-type sequence of the cell or cell line. In certain embodiments, the cell comprises genetically modified RBC precursors (hematopoietic stem cells known as "HSCs"). The cell or cell lines may be heterozygous or homozygous for the modification. The modifications may comprise insertions, deletions and/or combinations thereof. In certain embodiments, the HSCs are modified with an engineered nuclease and a donor nucleic acid such that a wild type gene (e.g., globin gene) is inserted and expressed and/or an endogenous aberrant gene is corrected. In certain embodiments, the modification (e.g., insertion) is at or near the nuclease(s) binding and/or cleavage site(s), for example, within 1-300 (or any value therebetween) base pairs upstream or downstream of the site(s) of cleavage, more preferably within 1-100 base pairs (or any value therebetween) of either side of the binding and/or cleavage site(s), even more preferably within 1 to 50 base pairs (or any value therebetween) on either side of the binding and/or cleavage site(s). In some cases, the wild type gene sequence for insertion encodes a wild type β globin. In other cases, the endogenous aberrant gene is the β globin gene, for example one or more genomic modifications that correct at least one mutation in an endogenous aberrant human beta-hemoglobin (Hbb) gene. In some aspects, the modification of the beta globin gene allows proper splicing of transcribed RNAs. In some cases, the region for correction comprises the IVS 1-1, 1-5, 1-6, 1-110 mutations. In a preferred embodiment, the beta globin region that is corrected comprises the IVS 1-1 mutation. In some embodiments, the region for correction comprises IVS 2-1, 2-745, or 2-654 mutations. Partially or fully differentiated cells descended from the modified stem cells as described herein are also provided (e.g., RBCs or RBC precursor cells). Compositions such as pharmaceutical compositions comprising the genetically modified cells as described herein are also provided.

In another aspect, described herein is a method for correcting or inserting a sequence into an endogenous gene (e.g., a beta globin gene) in a cell (e.g., stem cell), the method comprising cleaving the endogenous gene using one or more nucleases and correcting or inserting a sequence into the cleavage site. In certain embodiments, a genomic sequence in any target gene is replaced, for example using a ZFN or TALEN pair, or a CRIPSR/Cas system (or vector encoding said ZFN, TALEN and/or CRIPSR/Cas system) as described herein and a "donor" sequence (in some embodiments also known as a "transgene") that is inserted into the gene following targeted cleavage with the ZFN, TALEN and/or a CRIPSR/Cas system. The donor sequence may be present in the ZFN or TALEN vector, present in a separate vector (e.g., Ad, AAV or LV vector) or, alternatively, may be introduced into the cell using a different nucleic acid delivery mechanism. Such insertion of a donor nucleotide sequence into the target locus (e.g., globin gene, other safe-harbor gene, etc.) results in the expression of the transgene under control of the target locus's (e.g. globin's) genetic control elements. In some embodiments, the transgene encodes a non-coding RNA (e.g., an shRNA).

In other aspects, genetically modified RBC precursors (hematopoietic stem cells known as "HSCs") are given in a bone marrow transplant and the RBCs differentiate and mature in vivo. In some embodiments, the HSCs are isolated following G-CSF-induced mobilization, and in others, the cells are isolated from human bone marrow or umbilical cords. In some embodiments, the modified HSCs are administered to the patient following mild myeloablative preconditioning. In other aspects, the HSCs are administered after full myeloablation such that following engraftment, 100% of the hematopoietic cells are derived from the modified HSCs. In yet another aspect, provided herein are cell lines and/or transgenic animal models (systems). In some embodiments, the transgenic cell and/or animal includes a transgene that encodes a human gene. In some instances, the transgenic animal comprises a knock-out at the endogenous locus corresponding to exogenous transgene (e.g., the mouse globin gene is knocked out and the human globin gene is inserted into a mouse), thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., globin or safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

In a still further aspect, provided herein is a method for site specific integration of a nucleic acid sequence into an endogenous locus or correction of an endogenous gene at a desired locus (e.g., globin gene) of a chromosome, for example into the chromosome of an embryo. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger, TALE or Cas9 nuclease. In the case of using a Cas9 protein, an engineered single guide (sg)RNA is also introduced. The nuclease or nuclease system recognizes the target site in the target locus (e.g., globin or safe harbor locus), and then (b) the embryo is cultured to allow expression of the zinc finger or TALE nuclease and/or CRISPR/Cas system, wherein a double stranded break is introduced into the target by the zinc finger nuclease, TALEN or CRISPR/Cas system is then repaired, via homologous recombination with the DNA vector, so as to integrate the nucleic acid sequence into the chromosome.

In any of the methods described herein, the polynucleotide encoding the zinc finger nuclease(s), TALEN(s) and/or CRIPSR/Cas system can comprise DNA, RNA or combinations thereof. In certain embodiments, the polynucleotide comprises a plasmid. In other embodiments, the polynucleotide encoding the nuclease comprises mRNA.

A kit, comprising the ZFPs, TALENs and/or CRIPSR/Cas system of the invention, is also provided. The kit may comprise nucleic acids encoding the ZFPs, TALENs or CRISPR/Cas system, (e.g. RNA molecules or ZFP, TALEN or Cas9 encoding genes contained in a suitable expression vector) and engineered sg RNA if needed, or aliquots of the nuclease proteins, donor molecules, suitable host cell lines, instructions for performing the methods of the invention, and the like.

Thus, the disclosure includes, but is not limited to, a genetically modified cell comprising a genomic modification. In one embodiment, the genomic modification corrects at least one mutation in an endogenous aberrant human beta-hemoglobin (Hbb) gene. In a further embodiment, the genomic modification is selected from the group consisting of insertions, deletions and combinations thereof. In a related embodiment, the genetically modified cell is made by a nuclease including one of more of the nucleases disclosed herein (e.g., ZFN (e.g., as disclosed in the last two rows of Table 1), TALEN, etc.), which nuclease may be introduced in nucleic acid and/or protein form. In certain embodiments, the mutation is in an intervening sequence 1, mutation number 1 (IVS1-1) mutation, an IVS1-5 mutation, an IVS1-6 mutation, an IVS1-110 mutation, an IVS2-1 mutation, an IVS2-745 mutation or an IVS2-654 mutation. In other embodiments, the genomic modification corrects a point mutation. In still further embodiments, the invention comprises the genetically modified cell described above, wherein the genomic modification is within one or more of the sequences shown in SEQ ID NO:3, for example, a genomic modification within SEQ ID NO: 3 disrupts a splice donor motif. In still further embodiments, the GT dinucleotide at the beginning of intron 1 of the human beta-globin gene is changed to an AT. In still further embodiments, the genomic modification corrects a mutation that alters the splice donor site for mRNA processing of the aberrant Hbb gene that leads to beta-thalassemia. In still further embodiments, the genomic modification is at or near any of the sequences shown as SEQ ID Nos. 4 or 5. In still further embodiments, the genomic modification comprises insertion of donor sequence comprising a novel restriction enzyme cleavage site with respect to the endogenous Hbb gene. In certain embodiments, the donor sequence is between 2 kb to 200 kb in length, for example, a donor sequence selected from any one of SEQ ID Nos. 20 and 22 and the novel restriction enzyme cleavage site is an Xba I site. In certain embodiments, the donor sequence comprises a transgene of any length.

Any of the genetically modified cells has described herein may be, for example, a stem cell such as a hematopoietic stem cell (e.g., CD34+). Furthermore, described herein is a genetically modified differentiated cell descended from any of the genetically modified stem cells as described herein, including, for example, a red blood cell (RBC).

Also provided is a pharmaceutical composition comprising one of more of the genetically modified cells as described herein.

In addition, a zinc finger protein comprising 4, 5, or 6 zinc finger domains comprising a recognition helix region, each zinc finger domain comprising the recognition helix regions in the order shown in the last two rows of Table 1 is also provided. In certain embodiments, a fusion protein comprising a zinc finger protein and a wild-type or engineered cleavage half-domain is provided. Polynucleotides encoding any of the ZFPs and/or fusion proteins described herein are also provided. Described herein are isolated cells (e.g., red blood cells (RBCs) or precursor cells (e.g., CD4+ hematopoietic stem cells) comprising one or more the ZFPs, fusion proteins and/or polynucleotides described herein are also provided. Kits comprising a polynucleotide, a protein and/or cell as described herein are also provided.

Also described is a method of altering Hbb expression in a cell, the method comprising: introducing, into the cell, one or more polynucleotides as described herein, under conditions such that the one or more proteins are expressed and expression of the Hbb gene is altered (e.g., increased). In certain embodiments, the methods further comprise integrating a donor sequence into the genome of the cell, for example using a viral vector, as an oligonucleotide and/or on a plasmid. The donor sequence may comprise a transgene and expression of the transgene may be under the control of an endogenous or exogenous promoter. In other embodiments, the donor comprises an oligonucleotide that corrects a mutation that alters the splice donor site for mRNA processing of the Hbb gene. In certain embodiments, the cell is a red blood cell (RBC) precursor cell and/or a hematopoietic stem cell. In certain embodiments, the methods comprise producing a genetically modified cell comprising a genomic modification within an endogenous Hbb gene, the method comprising the steps of: a) contacting a cell with a polynucleotide encoding a fusion protein comprising a zinc finger nuclease comprising 4, 5, or 6 zinc finger domains, each zinc finger domain comprising a recognition helix region and further wherein the recognition helix regions are in the order shown in one of the last two rows of Table 1; b) subjecting the cell to conditions conducive to expressing the fusion protein from the polynucleotide; and c) modifying the endogenous Hbb gene with the expressed fusion protein sufficient to produce the genetically modified cell. In any of the methods described herein, the methods may further comprise stimulating the cells with at least one cytokine. The polynucleotide may delivered inside the cell, for example, using at least one of a non-viral delivery system, a viral delivery system, and/or a delivery vehicle. In certain embodiments, the methods involve subjecting the cells to an electric field.

Also described is a method of treating a patient with β-thalassemia, the method comprising administering to the patient the pharmaceutical preparation as described herein (e.g., a pharmaceutical composition describes one or more proteins, polynucleotides and/or cells as described herein) in an amount sufficient to increase the Hbb gene expression in the patient.

These and other aspects will be readily apparent to the skilled artisan in light of disclosure as a whole.

BRIEF DESCRIPTION OF THE DRAWINGS

FIG. 1 is an illustration of the human beta-globin gene structure, adapted from Kazazian and Boehm (1998) ibid. Across the top is the illustration of the beta globin gene where the hatched areas indicate the exons, and the clear areas depict the introns as well as the 5' and 3' non-coding regions. Also depicted are several of the known types of beta globin mutations associated with thalessemias, where an open balloon marker indicates mutations that effect splicing, closed balloons indicate transcriptional mutations, open squares indicate the cap site mutation, downward arrow indicates RNA cleavage mutations, upward filled arrows indicate frameshift mutations, upward open arrows indicate nonsense mutations, a block with an asterisk in it indicates mutations that increase mRNA instability, and the open rectangles indicate observed deletion mutations. The bottom panel of FIG. 1 (SEQ ID NO:1) depicts the location of the IVS 1-1 mutation and the wild type sequence corresponding to this sequence. Also shown are the binding locations for two ZFNs to cleave at or near the IVS 1-1 mutation, and the point mutation responsible for the IVS 1-1 mutation is indicated by an open bracket. FIG. 1 discloses encoded protein sequence as SEQ ID NO: 25.

FIG. 2A is a gel showing cleavage activity of the ZFN pair in human CD34+ cells using the Cel I Surveyor Assay, while FIG. 2B is a graph depicting cleavage at either the wild type ("wt") or the IVS 1.1 mutant sequence as measured by the Dual-Luciferase Single Strand Annealing Assay (See U.S. Pat. No. 8,586,526). The experiments shown in FIG. 2B are duplicates. Control experiments were done with cells transduced with a GFP reporter plasmid ("GFP") or sham transfected cells ("negative"). The data indicates that both alleles are cleaved by the ZFN pair.

FIGS. 3A and 3B depict schematics for introducing a IVS 1-1 mutation into a wild type beta globin gene. FIG. 3A depicts the steps of the gene modification where the wild type sequence in the endogenous beta globin gene is replaced with the IVS 1-1 mutation. The donor is a single stranded oligonucleotide comprising the IVS 1-1 mutation (depicting the A point mutation) as well as an XbaI restriction site ("ss oligonucleotide"), and the ZFN cleavage site. The cleaved endogenous gene (depicting the wild type G) is shown below the donor nucleotide, and the "gene corrected" endogenous gene, now comprising both the IVS 1-1 mutation and the Xba1 restriction site, is shown on the bottom. FIG. 3B (SEQ ID NO:2) is a close up of the ss oligonucleotide donor, showing the sequence around the ZFN cleavage site as well as the bracketed introduced nucleotides (SEQ ID NOS 26 and 27).

FIG. 4 depicts the results of the introduction of the IVS 1-1 mutation described in FIG. 3 into the wild type beta globin gene in normal CD34+ cells. Shown is a gel depicting the cleavage results from the introduced XbaI restriction enzyme (RFLP). The enzyme cleavage indicates that the CD34+ cells were "corrected" with either a ss oligonucleotide donor comprising the wild type ("wt") or IVS 1-1 beta globin sequence and an XbaI restriction site. Also shown below the gel are the results from high throughput sequencing of PCR products that comprise this region in the treated cells. Indicated is the amount of targeted integration of the donor in samples receiving the donor ("% TI"), and the amount of ZFN activity ("% indels") in the samples.

FIGS. 6A and 6B depict results following gene correction in patient-derived CD34+ cells. Beta thalassemia patient ("p13" shown in FIG. 6B)-derived CD34+ cells, along with wild type CD34+ cells ('WT' shown in FIG. 6A) were treated with an oligonucleotide to correct the IVS 1-1 mutation into wild type. Cells were treated with either pairs of ZFNs alone, with ZFNs plus gene correcting donor oligo ("WT oligo") or with donor oligo and GFP alone. In most instances, the donor oligo also comprised a unique XbaI restriction site ("XbaI"). The gels depict XbaI cleavage of genomic DNA isolated from the treated cells, and demonstrate insertion of the donor oligonucleotide. Lane designations are as follows: Lane 1 shows results using ZFNs 43545/43544; Lane 2 shows results using ZFNs 43545/45946; Lane 3 shows results using ZFNs 43545/45952; Lane 4 shows results using ZFNs 43545/43544 and WT oligo XbaI; Lane 5 shows results using ZFNs 43545/45946 and WT oligo XbaI; Lane 6 shows results using ZFNs 43545/45952 and WT oligo XbaI; Lane 7 shows results using GFP and WT oligo XbaI; Lane 8 shows results using ZFNs 43545/43544 and WT Oligo (p13 only); and Lane 9 shows results of untransfected cells.

DETAILED DESCRIPTION

Figure 2B:
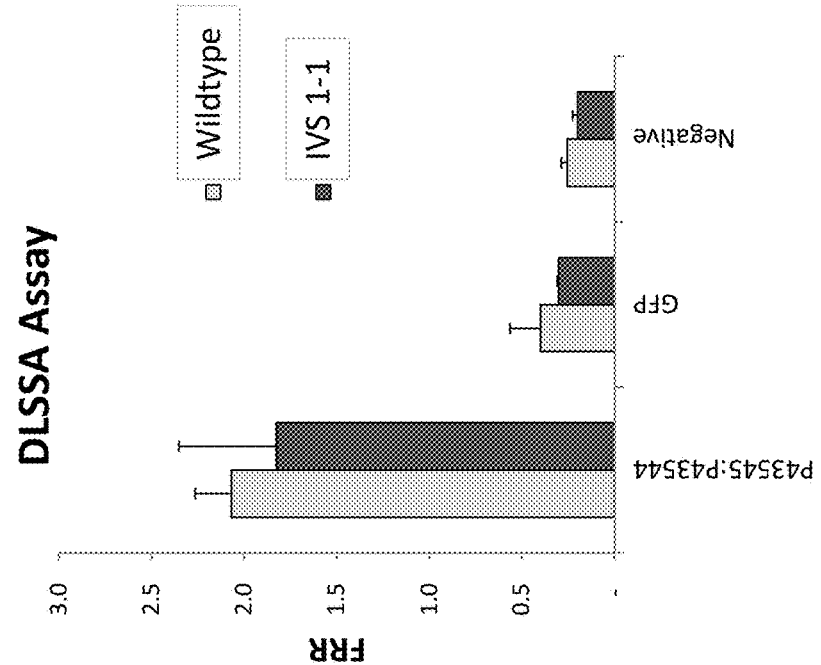
FIGS. 2A and 2B depict the activity of ZFN pair 43545/43544.

Disclosed herein are methods and compositions for studying and treating a genetic disease such as a hemoglobinopathy. The invention describes genomic editing of a target cell such that there is a favorable change in the production of one or more globin genes, which in turn results in treatment of hemoglobinopathies such as a thalassemia in a subject in need thereof. Favorable changes in the production of globin includes, but is not limited, correction of an aberrant β globin gene sequence. Additionally, delivery of altered hematopoietic stem cells in a transplant altered to express a desired protein product can be similarly beneficial in treating hemoglobinopathies such as a thalassemia. Also described are cell lines and animals with altered globin production.

Thus, the methods and compositions of the invention can be used to alter the production of one or more globin genes (e.g. β) in a cell (e.g., an erythroid precursor cell). These alterations and the methods and compositions can be used to edit an endogenous gene or insert a gene at a desired location in the genome of a cell (e.g., into an HSC). Precursor cells can be derived from subjects in need, modified ex vivo, and then given back to the subject either in a bone marrow graft.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 8,586,526; 5,789,538; 5,925,523; 6,007,988; 6,013,453; and 6,200,759.

"TtAgo" is a prokaryotic Argonaute protein thought to be involved in gene silencing. TtAgo is derived from the bacteria *Thermus thermophilus*. See, e.g., Swarts et al (2014) *Nature* 507(7491):258-61, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides. For the purposes of this disclosure, "homologous recombination" (HR) refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell. In addition, a CRISPR/Cas system may be similarly employed to induce additional double strand breaks.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598 and 8,823,618, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "disease associated gene" is one that is defective in some manner in a monogenic disease. Non-limiting examples of monogenic diseases include severe combined immunodeficiency, cystic fibrosis, lysosomal storage diseases (e.g. Gaucher's, Hurler's, Hunter's, Fabry's, Neimann-Pick, Tay-Sach's, etc.), sickle cell anemia, and thalassemia.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. An "aberrant" gene is a gene that differs in nucleotide sequence from the wild-type gene, including a gene that includes one or more mutations (e.g., point mutations, insertions and/or deletions) as compared to the wild-type sequence. Wild-type Hbb is disclosed, for example, in GenBank Accession No. NG_000007 (see, also, Efstratiadis et al. (1980) *Cell* 21(3):653-668). The product encoded by an aberrant gene may exhibit the same or different function (e.g., increased function, decreased function, no function) as compared to the product of the wild-type gene. Exemplary aberrant Hbb genes are disclosed herein and in Kazazian and Boehm (1988) *Blood* vol 71 No 4: 1107.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Red Blood Cells" (RBCs), or erythrocytes, are terminally differentiated cells derived from hematopoietic stem cells. They lack a nuclease and most cellular organelles. RBCs contain hemoglobin to carry oxygen from the lungs to the peripheral tissues. In fact, 33% of an individual RBC is hemoglobin. They also carry $CO_2$ produced by cells during metabolism out of the tissues and back to the lungs for release during exhale. RBCs are produced in the bone marrow in response to blood hypoxia which is mediated by release of erythropoietin (EPO) by the kidney. EPO causes an increase in the number of proerythroblasts and shortens the time required for full RBC maturation. After approximately 120 days, since the RBC do not contain a nucleus or any other regenerative capabilities, the cells are removed from circulation by either the phagocytic activities of macrophages in the liver, spleen and lymph nodes (~90%) or by hemolysis in the plasma (~10%). Following macrophage engulfment, chemical components of the RBC are broken down within vacuoles of the macrophages due to the action of lysosomal enzymes.

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE or Cas DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the altered RBCs (or stem cells) of the invention can be administered. Subjects of the present invention include those that have been exposed to one or more chemical toxins, including, for example, a nerve toxin.

Nucleases

Described herein are compositions, particularly nucleases, which are useful targeting a gene for use with hemoglobinopathies. In certain embodiments, the nuclease is naturally occurring. In other embodiments, the nuclease is non-naturally occurring, i.e., engineered in the DNA-binding domain and/or cleavage domain. Any DNA-binding domain can be used in the nucleases described herein. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains), or a generic nuclease guided by a specific guide RNA (e.g. a CRPISR/Cas).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG family ("LAGLIDADG" disclosed as SEQ ID NO: 23), the GIY-YIG family, the His-Cyst box family and the HNH family Exemplary homing endonucleases include I-SceI, I-CeuI, PI-P spI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et at (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et at (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et at (2007) *Appl and Envir Micro* 73(13): 4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of *Xanthomonas*.

Thus, in some embodiments, the DNA binding domain that binds to a target site in a target locus (e.g., globin or safe harbor) is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and *Ralstonia* (see Heuer et at (2007) *Applied and Environmental Microbiology* 73(13): 4379-4384); U.S. Pat. Nos. 8,420,782 and 8,440,431 and U.S. Patent Publication No. 20110301073.

In certain embodiments, the DNA binding domain comprises a zinc finger protein (e.g., a zinc finger protein that binds to a target site in a globin or safe-harbor gene). Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599, 692; 6,503,717; 6,689,558; 7,030,215; 6,794,136; 7,067, 317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding or TALE domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453, 242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins or TALE domains) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The DNA binding proteins described herein may include any combination of suitable linkers between the individual zinc fingers of the protein. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 8,586,526; 7,888,121; 6,140,081; 5,789,538; 6,453,242; 6,534,261; 5,925,523; 6,007,988; 6,013,453; 6,200,759.

In addition, as disclosed in these and other references, DNA-binding domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to safe harbor and other genes are disclosed for example, in U.S. application Ser. No. 14/278,903.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, the nuclease can comprise any DNA-binding domain that specifically binds to a target site in any gene.

B. Cleavage Domains

Any suitable cleavage domain can be operatively linked to any DNA-binding domain (e.g., ZFP, TALE, guide RNA, etc.) to form a nuclease or nuclease system. For example, ZFP, TALE, meganuclease, RNAs and other DNA-binding domains have been fused to nuclease domains to create nucleases—a functional entity that is able to recognize its intended nucleic acid target through its engineered DNA binding domain and cause the DNA to be cut at or near the binding site via the nuclease activity. Engineered nucleases including zinc finger nucleases ("ZFNs"), TALENs, CRISPR/Cas nuclease systems, and homing endonucleases that are all designed to specifically bind to target DNA sites have the ability to regulate gene expression of endogenous genes and are useful in genome engineering and gene therapy, including in the inactivation of HIV receptors such as CCR5 and CXCR4. See, e.g., U.S. Pat. Nos. 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and U.S. application Ser. No. 14/278,903, the disclosures of which are As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,888,121; 7,914,796; 8,034,598 and 8,823,618, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. No. 7,914,796, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Pat. No. 8,623,618, incorporated by reference herein). Engineered cleavage half-domains described herein can be prepared using any suitable method, for example, by site-directed mutagenesis of wild-type cleavage half-domains (Fok I) as described in U.S. Pat. Nos. 7,888,121; 7,914,796; 8,034,598 and 8,823,618.

Alternatively, nucleases may be assembled in vivo at the nucleic acid target site using so-called "split-enzyme" technology (see, e.g., U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Target Sites

As described in detail above, DNA-binding domains can be engineered to bind to any sequence of choice in a locus, for example a globin or safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Patent Publication No. 20110287512.

Donors

As noted above, insertion of an exogenous sequence (also called a "donor sequence" or "donor" or "transgene"), for example for correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805, 20110281361, 20110207221 and 20130326645. The donor sequence(s) can be contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. If introduced in double-stranded form, the donor may include one or more nuclease target sites, for example, nuclease target sites flanking the transgene to be integrated into the cell's genome. See, e.g., U.S. Patent Publication No. 20130326645.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)). Suitable non-viral vectors include nanotaxis vectors, including vectors commercially available from InCellArt (France).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 1 target site, for example, for use with a CRISPR/Cas, or 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into a globin locus such that some or none of the endogenous globin sequences are expressed, for example as a fusion with the transgene. In other embodiments, the transgene (e.g., with or without globin encoding sequences) is integrated into any endogenous locus, for example a safe-harbor locus. See, e.g., US patent publications 20080299580; 20080159996 and 201000218264.

When additional (e.g., globin sequences, endogenous or part of the transgene) are expressed with the transgene, the additionally (e.g., globin) sequences may be full-length sequences (wild-type or mutant) or partial sequences. Preferably, the additional sequences are functional. Non-limiting examples of the function of these full length or partial additional sequences, for example globin-encoding sequences, include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type beta globin gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger or TALEN protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds.) (1995); and Yu et al., Gene Therapy 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) Nature Biotechnology 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo).

Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SW), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72: 8463-8471; Zuffery et al. (1998) *J. Virol.* 72:9873-9880; Follenzi et al. (2000) *Nature Genetics* 25:217-222; U.S. Patent Publication No 20090117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by a plasmid, while the one or more nucleases can be carried by an AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example treatment of hemoglobinopathies via nuclease-mediated integration of a gene encoding a globin protein. The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Cells

Also described herein are cells and/or cell lines in which an endogenous sequence human beta-hemoglobin (Hbb) is modified. The modification may be, for example, as compared to the wild-type sequence of the cell, which may be a cell from a subject with a thalassemia. The cell or cell lines may be heterozygous or homozygous for the modification. The modifications are may comprise insertions, deletions and/or combinations thereof.

The Hbb gene may be modified by a nuclease (e.g., ZFN, TALEN, CRISPR/Cas system, Ttago system, etc.), for example a nuclease as described herein. In certain embodiments, the genomic modification is to an intervening sequence 1, mutation number 1 (IVS1-1 or IVS.1), IVS1-5, IVS1-6, IVS1-110, IVS-1, IVS2-745 or IVS2-654 mutation, for example a modification that corrects a mutant IVS.1 sequence as seen in subjects with a thalassemia such as beta-thalassemia. In certain embodiments, the invention comprises the genetically modified cell described above, wherein the genomic modification is within one or more of the sequences shown in SEQ ID NO:3, for example that disrupts a splice donor motif (e.g., modification of a "GT" dinucleotide at the beginning of intron 1 of the human beta-globin gene is modified to an "AT"). In certain embodiments, the genomic modification corrects a mutation that alters the splice donor site for mRNA processing of the Hbb gene and leads to beta-thalassemia.

The modification is preferably at or near the nuclease(s) binding and/or cleavage site(s), for example, within 1-300 (or any value therebetween) base pairs upstream or downstream of the site(s) of cleavage, more preferably within 1-100 base pairs (or any value therebetween) of either side of the binding and/or cleavage site(s), even more preferably within 1 to 50 base pairs (or any value therebetween) on either side of the binding and/or cleavage site(s). In certain embodiments, the modification is at or near any target sequence shown in SEQ ID NO:3, 4 or 5.

Any cell or cell line may be modified, for example a stem cell, for example an embryonic stem cell, an induced pluripotent stem cell, a hematopoietic stem cell, a neuronal stem cell and a mesenchymal stem cell. Other non-limiting examples of cells as described herein include T-cells (e.g., CD4+, CD3+, CD8+, etc.); dendritic cells; B-cells. A descendent of a stem cell, including a partially or fully differentiated cell, is also provided (e.g., a RBC or RBC precursor cell). Non-limiting examples other cell lines including a modified BCL11A sequence include COS, CHO (e.g., CHO-S, CHOK1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*.

The cells as described herein are useful in treating and/or preventing a disorder, for example, by ex vivo therapies. The nuclease-modified cells can be expanded and then reintroduced into the patient using standard techniques. See, e.g., Tebas et at (2014) *New Eng J Med* 370(10):901. In the case of stem cells, after infusion into the subject, in vivo differentiation of these precursors into cells expressing the functional transgene also occurs. Pharmaceutical compositions comprising the cells as described herein are also provided. In addition, the cells may be cryopreserved prior to administration to a patient.

Any of the modified cells or cell lines disclosed herein may show increased expression of a wild-type or inserted. Compositions such as pharmaceutical compositions comprising the genetically modified cells as described herein are also provided Applications The methods and compositions disclosed herein are for modifying expression of protein, or correcting an aberrant gene sequence in a genetic disease, such as a thalassemia.

Thus, the methods and compositions provide for the treatment and/or prevention of such genetic diseases. Genome editing, for example of stem cells, is used to correct an aberrant gene, insert a wild type gene, or change the expression of an endogenous gene. By way of non-limiting example, a wild type gene, e.g. encoding at least one globin (e.g. β globin), may be inserted into a cell to provide the globin proteins deficient and/or lacking in the cell and thereby treat a genetic disease, e.g., a hemoglobinopathy. Alternatively or in addition, genomic editing with or without administration of the appropriate donor, can correct the faulty endogenous gene, e.g., correcting the point mutation in β-hemoglobin, to restore expression of the gene and/or treat a genetic disease, e.g. beta-thalassemia.

The following Examples relate to exemplary embodiments of the present disclosure in which the nuclease comprises a zinc finger nuclease (ZFN). It will be appreciated that this is for purposes of exemplification only and that other nucleases can be used, for instance TALENs, homing endonucleases (meganucleases) with engineered DNA-binding domains and/or fusions of naturally occurring of engineered homing endonucleases (meganucleases) and DNA-binding domains and heterologous cleavage domains, (e.g. Mega-TAL) and/or a CRISPR/Cas system comprising an engineered single guide RNA.

EXAMPLES

Example 1: Design, Construction and General Characterization of Zinc Finger Protein Nucleases (ZFN)

Zinc finger proteins were designed and incorporated into plasmids, AAV or adenoviral vectors essentially as described in Urnov et al. (2005) *Nature* 435(7042):646-651, Perez et at (2008) *Nature Biotechnology* 26(7):808-816, and as described in U.S. Pat. No. 6,534,261. For ZFNs and TALENs specific for the human beta globin locus see, also, co-owned U.S. Pat. No. 7,888,121.

Example 2: Activity of Beta Globin-Specific ZFNs

ZFN pairs targeting the human beta globin locus at or near the IVS1-1 mutation were made as described above. See, also, U.S. Patent Publication No. 20140093913. The amino acid sequences of the recognition helix regions of each finger of the indicated ZFNs are shown below in Table 1 along with the whole target sites (DNA target sites indicated in uppercase letters; non-contacted nucleotides indicated in lowercase). The location of the target site is also shown in FIG. 1. All ZFPs were tested for binding specificity to their target sequence.

TABLE 1

Zinc finger nucleases

| SBS #, Target | Design Human B-Hemoglobin IVS1-1 region specific ZFNs | | | | | |
|---|---|---|---|---|---|---|
| | F1 | F2 | F3 | F4 | F5 | F6 |
| SBS#43544 aTCTGCCCAGGGCC TCaccaccaactt (SEQ ID NO: 4) | AMQTLRV (SEQ ID NO: 6) | DRSHLAR (SEQ ID NO: 7) | RSDNLSE (SEQ ID NO: 8) | ASKTRKN (SEQ ID NO: 9) | RNSDRTK (SEQ ID NO: 10) | N/A |

TABLE 1-continued

Zinc finger nucleases

Human B-Hemoglobin IVS1-1 region specific ZFNs

| SBS #, Target | F1 | F2 | F3 | F4 | F5 | F6 |
|---|---|---|---|---|---|---|
| SBS#43545<br>atCAAGGTTACAAG<br>ACAGGTttaaggag<br>(SEQ ID NO: 5) | LRHHLTR<br>(SEQ ID<br>NO: 11) | QSGTRKT<br>(SEQ ID<br>NO: 12) | RSDNLST<br>(SEQ ID<br>NO: 13) | DSANRIK<br>(SEQ ID<br>NO: 14) | LRHHLTR<br>(SEQ ID<br>NO: 11) | QSGNLHV<br>(SEQ ID<br>NO: 15) |
| SBS#45946<br>aaTCTGCCCAGGGC<br>CTCaccaccaactt<br>(SEQ ID NO: 24) | AMQTLRV<br>(SEQ ID<br>NO: 16) | DRSHLAR<br>(SEQ ID<br>NO: 7) | RSDNLSE<br>(SEQ ID<br>NO: 8) | ASKTRKN<br>(SEQ ID<br>NO: 9) | TSSDRKK<br>(SEQ ID<br>NO: 17) | N/A |
| SBS#45952<br>aaTCTGCCCAGGGC<br>CTCaccaccaactt<br>(SEQ ID NO: 24) | AMQTLRV<br>(SEQ ID<br>NO: 16) | DRSHLAR<br>(SEQ ID<br>NO: 7) | RSDNLSE<br>(SEQ ID<br>NO: 8) | ASKTRKN<br>(SEQ ID<br>NO: 9) | VYEGLKK<br>(SEQ ID<br>NO: 18) | N/A |

The Cel-I assay (Surveyor™, Transgenomics) as described in Perez et al. (2008) *Nat. Biotechnol.* 26: 808-816 and Guschin et al. (2010) *Methods Mol Biol.* 649:247-56), was used to detect ZFN-induced modifications of the target gene in K562 or HSCs. In this assay, PCR-amplification of the target site was followed by quantification of insertions and/or deletions ("indels") using the mismatch detecting enzyme Cel-I (Yang et al. (2000) *Biochemistry* 39: 3533-3541) which provided a lower-limit estimate of DSB frequency. Three days following transfection of the ZFN expression vector at either standard conditions (37° C.) or using a hypothermic shock (30° C., see co-owned US patent publication U.S. Patent Publication No. 20110041195), genomic DNA was isolated from K562 cells using the DNeasy kit (Qiagen).

Figure 2A:
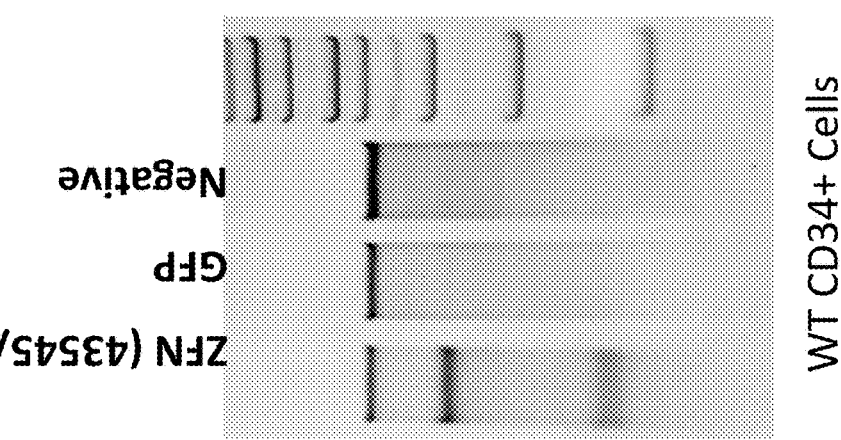

The results (FIG. 2A) from the Cel-I assay demonstrated that the ZFNs were capable of inducing cleavage at their respective target sites. In addition, the ZFNs were tested for activity using the Dual-Luciferase Single Strand Annealing Assay (DLSSA). This system was used to quantify ZFN activity in transiently transfected cells, and is based on the Dual-Luciferase Reporter® Assay System from Promega. The system sequential measures two individual reporter enzymes, Firefly and Renilla Luciferases, within a single tube (well). Both of the Firefly and the Renilla Luciferase reporters are re-engineered and the assay conditions are optimized. The Firefly Luciferase reporter construct contains two incomplete copies of the Firefly coding regions that are separated by DNA binding sites for the ZFNs. In this study, the 5' copy is derived from approximately two third of the N-terminal part of the Firefly gene and the 3' copy is derived from approximately two third of the C-terminal part of the Firefly gene. The two incomplete copies contain about 600-bp homology arms. The separated Firefly fragments have no luciferase activity. A DNA double strand break caused by the ZFN pair will stimulate recombination between flanking repeats by the single-strand annealing pathway and then restore the Firefly luciferase function. The co-transfected Renilla Luciferase plasmid provides an internal control. The luminescent activity of each reporter is read on a luminometer. Normalizing the activity of the experimental reporter (Firefly) to the activity of the internal control (Renilla) minimizes experimental variability caused by differences in cell viability and/or transfection efficiency. The normalized value is used to determine the activity of a given ZFN or TALEN pair.

The results (FIG. 2B) demonstrate that the 43545/43544 pair is capable of cleaving both the wild type beta globin sequence and the mutant IVS 1-1 sequence.

Example 3: Editing of the IVS 1-1 Beta Globin Locus

The human beta globin gene (HBB) specific ZFN 43545/43544 pair was used to introduce a donor DNA into the beta globin locus as follows. A donor oligo was designed for capture into the cleaved HBB gene following ZFN treatment. The oligo contained an XbaI restriction site such that following insertion of the oligo, a novel restriction site was introduced into the HBB gene intron (IVS1) right after the ZFN recognition site that could subsequently be visualized by restriction digest of a PCR product containing the ZFN binding region (see, FIG. 3).

The various oligos were delivered to CD34+ cells as single stranded molecules and are shown below:

Hbb oligo WT:
(SEQ ID NO: 19)
5'
AAGTCTGCCGTTACTGCCCTGTGGGGCAAGGTGAACGTGGATGAAGTTGG

TGGTGAGGCCCTGGGCAGGTTGGTATCAAGGTTACAAGACAGGTTTAAGG

AGACCAATAGAAACTGGGCATGTGGAGACAGA

Hbb oligo G_A:
(SEQ ID NO: 20)
5'
AAGTCTGCCGTTACTGCCCTGTGGGGCAAGGTGAACGTGGATGAAGTTGG

TGGTGAGGCCCTGGGCAGATTGGTATCAAGGTTACAAGACAGGTTTAAGG

AGACCAATAGAAACTGGGCATGTGGAGACAGA

Hbb oligo WT XbaI:
(SEQ ID NO: 21)
5'
AAGTCTGCCGTTACTGCCCTGTGGGGCAAGGTGAACGTGGATGAAGTTGG

TGGTGAGGCCCTGGGCAGGTTGGTATCTAGAGGTTACAAGACAGGTTTAA

GGAGACCAATAGAAACTGGGCATGTGGAGACAGA

-continued

Hbb oligo G_A XbaI:
(SEQ ID NO: 22)
5'
AAGTCTGCCGTTACTGCCCTGTGGGGCAAGGTGAACGTGGATGAAGTTGG

TGGTGAGGCCCTGGGCAGATTGGTATCTAGAGGTTACAAGACAGGTTTAA

GGAGACCAATAGAAACTGGGCATGTGGAGACAGA

For the CD34+ transduction, a BTX ECM830 device with a 2 mm gap cuvette was used. mRNAs from the cells were prepared using a mMessageMachine T7 Ultra Kit (#AM1345, Ambion). Human CD34+ cells were grown in x-vivo10 media (Lonza) with 1xCC110 (Stem cell Technology) in non-tissue culture treated plates. The cells were counted and collected by centrifugation at 1200 rpm for 10 minutes at room temperature. The cells were washed 1-2× with room temperature PBS. 200,000 cells were used for each transfection, and they were resuspended in 100 µL BTexpress solution. 2-4 µg mRNA was added per transfection and the mixture was transferred to the cuvette. Immediately following transfer, the mixture was electroporated at 250V for 5 msec. Pre-warmed media was added to the cuvette and the media plus cells were transferred to a 48 well non-tissue culture treated plates and then incubated at 37° C. Gene editing was measured by high-throughput DNA sequencing of PCR amplicons of the HBB gene. Percent gene modification by non-homologous end joining ("NHEJ", caused by the healing of a double stranded break in the DNA following ZFN-induced cleavage) or targeted integration of the oligo following ZFN cleavage ("gene correction") was analyzed.

As shown in FIG. 4, the β globin oligo donor was inserted into the proper locus, as verified by the presence of the novel restriction site present on the donor DNA. Furthermore, sequence analysis was performed to verify the percent of alleles comprising a targeted integration and/or indels (insertions and/or deletions) introduced by error-prone NHEJ following ZFN cleavage. Genomic DNA was extracted (using Qiagen QIAamp® DNA micro kit) and analyzed for ZFN activity as follows. Briefly, the region comprising the cleavage site was amplified by PCR by standard methods, and following amplification, the PCR product was sequenced via MiSeq high throughput sequencing analysis according to manufacturer's instructions (Illumina®).

To quantitate the percent of edited alleles, the genomic region of interest was PCR amplified using primers which add the standard Illumina® sequencing adapter sequences. A second group of 13 rounds of PCR was performed to add barcode and bridge adapter sequences to both ends. Sequencing was performed on an Illumina® MiSeq according to manufacturer's protocols for amplicon sequencing. The MiSeq generates paired-end reads, which are merged and adapter-trimmed using a standard alignment software. Reads were then demultiplexed by sample via barcode sequence pairs using custom scripts. Amplicon sequences were then globally aligned to a reference sequence via an implementation of the Needleman-Wunsch algorithm (Needleman, Saul B.; and Wunsch, Christian D. (1970). Jour Mol Bio 48 (3): 443-53). Gaps or insertions in the alignment were counted as % NHEJ events, and compared to an untreated control sample sequence to determine sequence-specific background rates.

For calculation of targeted integration, Amplicon sequences were globally aligned to a reference sequence via a biopython implementation of the Needleman-Wunsch algorithm (Needleman, Saul B.; and Wunsch, Christian D., ibid). Sequence changes generated via experimental treatments were searched for, counted, and compared to counts in control samples. Known single feature polymorphisms (SNPs) may be masked out during this process and excluded from further counts (e.g., 1-bp deletion SFPs close to the ZFN target site). The percent of non-homologous end joining (NHEJ %) (also referred to as indels) was calculated by determining the percentage of sequences that contain insertions and/or deletions. Samples treated only with GFP vector were used to assess the PCR and sequencing error based background frequency of insertions and deletions. Background frequencies of less than 1% were observed.

The results demonstrate that in the presence of the oligo donor and the ZFN pair, approximately 12-14% of the cells showed an integration event. In addition, analysis for the presence of indels showed that when ZFNs were present, indels were detected in 42-70% of the alleles. See, also, FIG. 4.

To differentiate the transgenic CD34+ cells into mature RBCs, methods known in the art were used. Pools of ZFN-modified CD34+ cells were induced to differentiate as described in Giarratana et al. (2011) Blood 118(19):5071-9.

Figure 5:
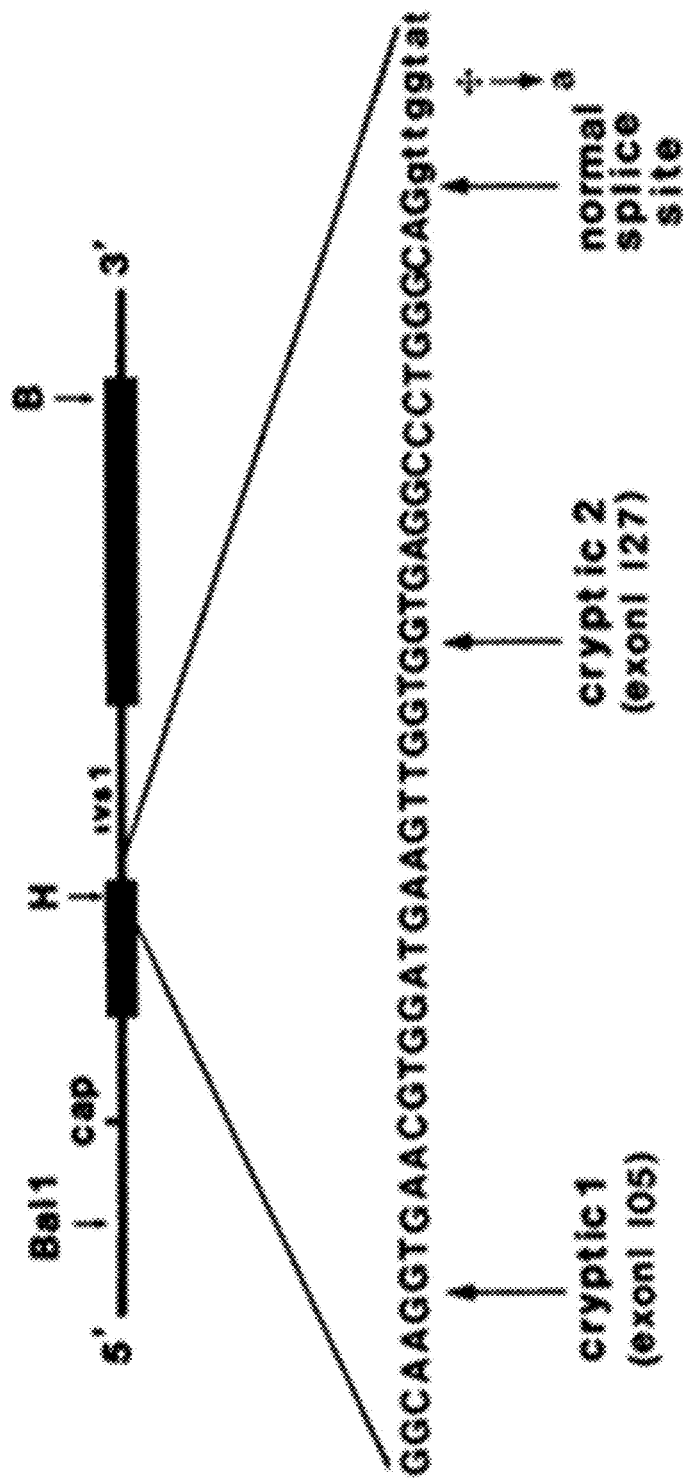
FIG. 5 depicts the genomic sequence (SEQ ID NO:3) around the IVS 1-1 mutation (Adapted from Lapoumeroulie et al, (1987) *Nucleic Acids Research*, 15(20): 8195). Indicated in the figure are cryptic splice sites that are used when the normal splice site is disrupted by the G→A IVS1-1 mutation.

At day 14 of erythrocyte differentiation, total RNA was isolated and splicing of the beta globin gene was analyzed via standard RT-PCR and sequence analysis as described above. The results (see Table 2) demonstrate that cleavage by the ZFNs alone is capable of introduction of indels that interfere with proper splicing, and this effect is also seen in the presence of the IVS 1-1 oligo donor, where a percent of splicing occurs via novel cryptic splicing sites (see FIG. 5). However, when the WT oligo donor is used, splicing is partially restored to the levels seen when ZFNs are not used. In addition, the presence of the introduced XbaI site in the oligo donor does not appear to affect splicing.

TABLE 2

Splicing products in treated erythrocytes

| Sample | Percent of splicing products | | | |
|---|---|---|---|---|
| | Normal | Cryptic 1 | Cryptic 2 | Other |
| ZFN only | 86.6 | 9.3 | 2.5 | 1.6 |
| ZFN + Oligo_G-A | 90.2 | 6.5 | 1.7 | 1.6 |
| ZFN + Oligo_G-A XbaI | 91.8 | 5.3 | 1.8 | 1.2 |
| ZFN + Oligo_WT XbaI | 94.4 | 3.9 | 0.9 | 0.8 |
| Oligo_G-A | 99.6 | 0.1 | 0.1 | 0.2 |
| Oligo_G-A XbaI | 99.7 | 0.1 | 0.1 | 0.1 |
| Oligo_WT XbaI | 99.7 | 0.1 | 0.1 | 0.2 |
| GFP | 99.7 | 0.1 | 0.1 | 0.2 |
| Untransfected | 99.3 | 0.3 | 0.2 | 0.3 |

Example 4: Oligo Based Gene Correction of the IVS1-1 Mutation in Thalassemia CD34+ Cells Thalassemia patient derived CD34+ cells were then treated to correct the IVS 1-1 mutation. This patient, "p13", is a β⁰β⁰ patient with the IVS1-1 mutation on one allele and a nonsense mutation (TGG→TAG) on the other allele at codon 15. CD34+ cells were isolated and treated with the nucleases and donor oligos as described in Example 3. In addition, high throughput sequencing analysis was performed to look at the modification caused by the nucleases and oligos. Genomic DNA was isolated from the samples and demonstrated that there was a high rate of cleavage with the XbaI restriction enzyme due to targeted integration of the oligo donor (see FIG. 6).

Sequence analysis is shown below in Table 3. The first set of data is for the WT CD34 cells where both beta globin alleles have wild type sequence, whereas the second data group is for the beta thalassemia p13 patient cells.

TABLE 3

Results following gene correction in CD34+ cells

| Cell Type | ZFNs | Oligo | % Indel | XbaI RFLP | % "G" at IVS11 site |
|---|---|---|---|---|---|
| WT C34 | 43545 + 43544 | none | 58.4 | 0.5 | 79.2 |
| | 43545 + 45946 | none | 18.1 | 0.3 | 94.2 |
| | 43545 + 45952 | none | 4.3 | 0.0 | 98.6 |
| | 43545 + 43544 | WT-XbaI | 37.5 | 9.7 | 91.0 |
| | 43545 + 45946 | WT-XbaI | 5.5 | 1.4 | 98.7 |
| | 43545 + 45952 | WT-XbaI | 1.0 | 0.1 | 99.8 |
| | GFP | WT-XbaI | 0.6 | 0.0 | 99.8 |
| | Untransfected | none | 0.1 | 0.0 | 99.9 |

| | ZFNs | Oligo | % Indel overall | XbaI RFLP overall | % "G" at IVS11 site on IVS1.1 allele | % Indel at IVS11 on IVS1.1 allele | % XbaI RFLP on IVS1.1 allele | % Indel at IVS11 site on codon15 allele | % XbaI-RFLP on codon15 allele |
|---|---|---|---|---|---|---|---|---|---|
| IVS1.1 P13 | 43545 + 43544 | none | 73.7 | 1.2 | 10.6 | 85.0 | 1.9 | 60.6 | 0.6 |
| | 43545 + 45946 | none | 39.8 | 0.8 | 11.6 | 67.2 | 1.4 | 22.4 | 0.5 |
| | 43545 + 45952 | none | 18.6 | 0.5 | 10.5 | 48.2 | 1.5 | 5.0 | 0.1 |
| | 43545 + 43544 | WT-XbaI | 55.9 | 21.7 | 34.6 | 82.7 | 29.5 | 37.6 | 16.6 |
| | 43545 + 45946 | WT-XbaI | 12.6 | 4.0 | 18.0 | 33.8 | 10.9 | 5.3 | 1.6 |
| | 43545 + 45952 | WT-XbaI | 3.2 | 0.9 | 13.9 | 11.6 | 3.4 | 0.9 | 0.3 |
| | GFP | WT-XbaI | 0.1 | 0.0 | 8.9 | 0.0 | 0.0 | 0.2 | 0.0 |
| | 43545 + 43544 | WT | 19.1 | 0.0 | 33.5 | 39.3 | 0.1 | 8.3 | 0.0 |
| | untransfected | none | 0.1 | 0.0 | 10.7 | 0.1 | 0.0 | 0.2 | 0.0 |

The data demonstrates activity of the nucleases at the IVS1-1 site in both cell populations, as measured by indel activity in the ZFN alone samples. In the presence of the donors comprising the XbaI site, there is a notable amount of RFLP detection, indicating integration of the donor oligo. In the p13 cells, use of the WT oligo donor that includes the XbaI site causes the appearance of the XbaI RFLP on both alleles. There is also an increase in WT sequence "G" at the IVS1-1 site on the IVS1-1 allele (for example, with the 43545/43544 ZFN pair, a value of 34.6% WT sequence was detected as compared to 10.7% in the untransfected cells.

Patient-derived CD34+ cells that have been ZFN-modified were induced to differentiate into colonies using Stemcell Technologies' Methocult methylcellulose medium according to manufacturer's directions. Differentiation was analyzed by assay of colony types arising from Methocult-induced differentiation: colony-forming units, erythroid ("CFU-E"); burst-forming units, erythroid ("BFU-E"); colony-forming units, granulocyte/macrophage ("CFU-GM") and colony-forming units; granulocyte/erythrocyte/monocyte/macrophage ("CFU-GEMM"). The BFU-E colonies were picked and analyzed for genotyping and beta-globin splicing using MiSeq analysis. 20% of all the clones have IVS1.1 mutation corrected to wild type "G", and the beta-globin splicing restored to normal. The data also confirmed that addition of the XbaI restriction site in the IVS1 intron has no adverse effect on beta-globin splicing.

Taken together, these data demonstrate successful gene correction of a mutation (the IVS1-1 mutation) in beta globin gene in beta thalassemia patient-derived CD34+ cells.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A genetically modified CD34+ stem cell comprising a corrected endogenous aberrant human beta-hemoglobin (Hbb) gene, a donor comprising the sequence of SEQ ID NO:19 or SEQ ID NO:21 and a pair of zinc finger nucleases comprising first and second zinc finger nucleases, wherein each zinc finger nuclease comprises 5 or 6 zinc finger domains, each zinc finger domain comprising a recognition helix region ordered F1 to F5 or F1 to F6, wherein the zinc finger nuclease (ZFN) comprises:
   (i) a first zinc finger nuclease that binds to a target site as shown in SEQ ID NO:5, the first ZFN comprising the following recognition helix regions:
   F1: LRHHLTR (SEQ ID NO:11);
   F2: QSGTRKT (SEQ ID NO:12);
   F3: RSDNLST (SEQ ID NO:13);
   F4: DSANRIK (SEQ ID NO:14);
   F5: LRHHLTR (SEQ ID NO:11); and
   F6: QSGNLHV (SEQ ID NO:15); and
   (ii) a second zinc finger nuclease that binds to a target site as shown in SEQ ID NO:4, the second ZFN comprising the following recognition helix regions:
   F1: AMQTLRV (SEQ ID NO:16);
   F2: DRSHLAR (SEQ ID NO:7);
   F3: RSDNLSE (SEQ ID NO:8);
   F4: ASKTRKN (SEQ ID NO:9); and F5: TSSDRKK (SEQ ID NO:17) or VYEGLKK (SEQ ID NO:18), wherein the donor sequence is integrated into an endogenous aberrant human beta-hemoglobin (Hbb) gene following targeted cleavage by the pair of zinc finger nucleases, thereby correcting the sequence of the Hbb gene.

2. The genetically modified cell of claim 1, wherein the aberrant Hbb gene comprises an intervening sequence 1, mutation number 1 (IVS1-1) mutation.

3. The genetically modified cell of claim 2, wherein the aberrant Hbb gene comprises a point mutation.

4. The genetically modified cell of claim 3, wherein the aberrant Hbb gene comprises a genomic modification within one or more of the sequences of SEQ ID NO:3.

5. The genetically modified cell of claim 4, wherein the genomic modification within SEQ ID NO: 3 disrupts a splice donor motif.

6. The genetically modified cell of claim 5, wherein the GT dinucleotide at the beginning of intron 1 of the human beta-globin gene is changed to an AT dinucleotide.

7. The genetically modified cell of claim 3, wherein the donor corrects a mutation that alters the splice donor site for mRNA processing of the aberrant Hbb gene that leads to beta-thalassemia.

8. The genetically modified cell of claim 3, wherein the donor sequence is integrated within any of the sequences of SEQ ID Nos. 4 or 5.

9. The genetically modified cell of claim 8, wherein the donor sequence comprises a novel restriction enzyme cleavage site with respect to the endogenous Hbb gene.

10. A genetically modified differentiated cell descended from the stem cell of claim 1.

11. The genetically modified cell of claim 10, wherein the cell is a red blood cell (RBC).

12. A pharmaceutical composition comprising the genetically modified cell of claim 1.

* * * * *

SEQUENCE LISTING

<160> NUMBER OF SEQ ID NOS: 27

<210> SEQ ID NO 1
<211> LENGTH: 51
<212> TYPE: DNA
<213> ORGANISM: Homo sapiens
<220> FEATURE:
<221> NAME/KEY: CDS
<222> LOCATION: (1)..(21)

<400> SEQUENCE: 1 gtt ggt ggt gag gcc ctg ggc aggttggtat caaggttaca agacaggttt        51
Val Gly Gly Glu Ala Leu Gly
1               5

<210> SEQ ID NO 2
<211> LENGTH: 44
<212> TYPE: DNA
<213> ORGANISM: Homo sapiens

<400> SEQUENCE: 2
gaggccctgg gcaggttggt atcaaggtta caagacaggt ttaa                    44

<210> SEQ ID NO 3
<211> LENGTH: 52
<212> TYPE: DNA
<213> ORGANISM: Homo sapiens

<400> SEQUENCE: 3
ggcaaggtga acgtggatga agttggtggt gaggccctgg gcaggttggt at           52

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atctgcccag ggcctcacca ccaactt                                       27

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atcaaggtta caagacaggt ttaaggag                                      28

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Met Gln Thr Leu Arg Val
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Arg Ser His Leu Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Asp Asn Leu Ser Glu
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ser Lys Thr Arg Lys Asn
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Asn Ser Asp Arg Thr Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Arg His His Leu Thr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 12

Gln Ser Gly Thr Arg Lys Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp Asn Leu Ser Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ser Ala Asn Arg Ile Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Gly Asn Leu His Val
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Met Gln Thr Leu Arg Val
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ser Ser Asp Arg Lys Lys
1               5
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Tyr Glu Gly Leu Lys Lys
1               5

<210> SEQ ID NO 19
<211> LENGTH: 132
<212> TYPE: DNA
<213> ORGANISM: Homo sapiens

<400> SEQUENCE: 19
aagtctgccg ttactgccct gtggggcaag gtgaacgtgg atgaagttgg tgtgaggcc      60 ctgggcaggt tggtatcaag gttacaagac aggtttaagg agaccaatag aaactgggca    120
tgtggagaca ga                                                        132

<210> SEQ ID NO 20
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
aagtctgccg ttactgccct gtggggcaag gtgaacgtgg atgaagttgg tgtgaggcc      60 ctgggcagat tggtatcaag gttacaagac aggtttaagg agaccaatag aaactgggca    120
tgtggagaca ga                                                        132

<210> SEQ ID NO 21
<211> LENGTH: 134
<212> TYPE: DNA
<213> ORGANISM: Homo sapiens

<400> SEQUENCE: 21
aagtctgccg ttactgccct gtggggcaag gtgaacgtgg atgaagttgg tgtgaggcc      60 ctgggcaggt tggtatctag aggttacaag acaggtttaa ggagaccaat agaaactggg    120
catgtggaga caga                                                      134

<210> SEQ ID NO 22
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
aagtctgccg ttactgccct gtggggcaag gtgaacgtgg atgaagttgg tgtgaggcc      60 ctgggcagat tggtatctag aggttacaag acaggtttaa ggagaccaat agaaactggg    120
catgtggaga caga                                                      134

```
<210> SEQ ID NO 23
<211> LENGTH: 9
<212> TYPE: PRT
<213> ORGANISM: Unknown
<220> FEATURE:
<223> OTHER INFORMATION: Description of Unknown: "LAGLIDADG" family
      motif peptide

<400> SEQUENCE: 23

Leu Ala Gly Leu Ile Asp Ala Asp Gly
1               5

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aatctgccca gggcctcacc accaactt                                       28

<210> SEQ ID NO 25
<211> LENGTH: 7
<212> TYPE: PRT
<213> ORGANISM: Homo sapiens

<400> SEQUENCE: 25

Val Gly Gly Glu Ala Leu Gly
1               5

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gaggccctgg gcagattggt atcaaggtta caagacaggt ttaa                     44

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaggccctgg gcaggttggt atctagaggt tacaagacag gtttaa                   46
```